US00PP13465P2

(12) United States Plant Patent
Apps

(10) Patent No.: US PP13,465 P2
(45) Date of Patent: Jan. 7, 2003

(54) DAYLILY PLANT NAMED 'SUNSET RETURNS'

(75) Inventor: Darrel A. Apps, Bridgeton, NJ (US)

(73) Assignee: Centerton Nursery, Inc., Bridgeton, NJ (US)

( * ) Notice: Subject to any disclaimer, the term of this patent is extended or adjusted under 35 U.S.C. 154(b) by 0 days.

(21) Appl. No.: 09/951,435

(22) Filed: Sep. 14, 2001

(51) Int. Cl.[7] ..... A01H 5/00
(52) U.S. Cl. ..... Plt./312
(58) Field of Search ..... Plt./312

*Primary Examiner*—Kent L. Bell
(74) *Attorney, Agent, or Firm*—Burns, Doane, Swecker & Mathis, LLP

(57) ABSTRACT

A new and distinct Hemerocallis cultivar of the dormant type named 'Sunset Returns' is provided. The new cultivar is very floriferous and forms attractive gold-pastel blossoms over an extended period of time that commonly begins during late May to early June and commonly ends during early to mid-October in USDA Hardiness Zone No. 7. The blossom coloration is Naples Yellow using terminology of the R.H.S. Colour Chart. The new plant readily forms fans and readily forms a number of scapes per fan. The new cultivar is particularly well suited for growing as distinctive colorful ornamentation in the landscape.

1 Drawing Sheet

BOTANICAL/COMMERCIAL CLASSIFICATION

*Hemerocallis hybrida/Daylily.*

Figure 1:
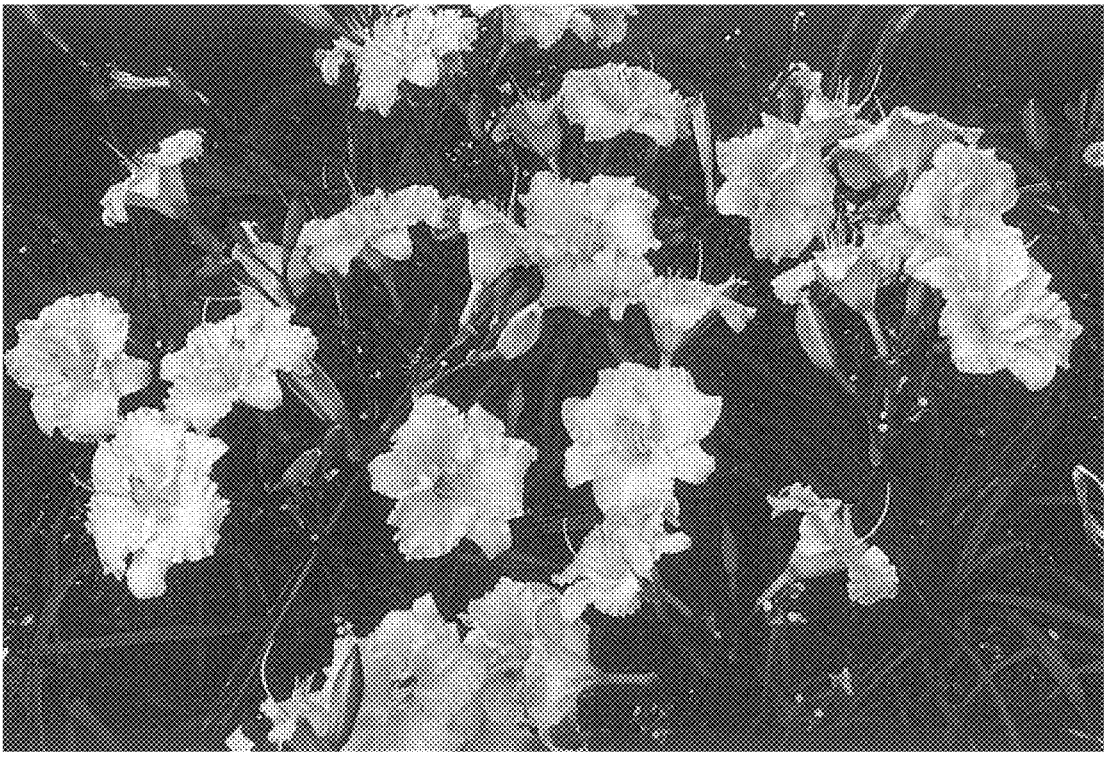

VARIETAL DENOMINATION cv. 'Sunset Returns'.

SUMMARY OF THE INVENTION

The present invention comprises a new and distinct cultivar of Hemerocallis of the dormant type, and hereinafter is referred to by the cultivar name 'Sunset Returns'.

The new cultivar is the product of a planned breeding program which had as its objective the creation of a new Daylily cultivar that is intended for use as attractive ornamentation in the landscape.

The cross that resulted in the production of the new cultivar of the present invention was carried out in a controlled environment during July, 1993, at Bridgeton, N.J., U.S.A. The female parent (i.e., the seed parent) of the new cultivar was the 'Sunny Honey' cultivar (non-patented in the United States) having golden yellow flowers which display a diameter of approximately 9 cm and fragile tepals that lack resistance to sunshine.

The male parent (i.e., the pollen parent) of the new cultivar was the 'Opportunity' cultivar (non-patented in the United States) having light creamy-yellow flowers which display a diameter of approximately 9 cm and fragile tepals that lack resistance to sunshine. The parent plants are registered with the American Hemerocallis Society.

The parentage of the new cultivar of the present invention can be summarized as follows:

'Sunny Honey'×'Opportunity'.

The seeds resulting from the above pollination were sown and small plantlets were obtained which were physically and biologically different from each other. A number of such plants were transplanted into the field at Bridgeton, N.J., U.S.A. during May 1994. Selective study during June 1994 resulted in the identification of a single plant of the new cultivar.

It was found that the new Hemerocallis cultivar of the present invention is of the dormant type and:

(a) Forms attractive gold-pastel flowers having a substantial substance and a funnel-shaped form,
(b) Possesses a long blooming season with substantially continuous blooming,
(c) Exhibits a propensity to readily display a plurality of fans, and
(d) Readily forms a plurality of scapes per fan over the flowering season.

The new cultivar of the present invention can be readily distinguished from its 'Sunny Honey' and 'Opportunity' parents. More specifically, the new cultivar forms smaller flowers, and bears foliage that is lower and deeper green when compared to each of the parental cultivars.

The 'Sunset Returns' cultivar resembles some well-known cultivars, such as the 'Stella D' Oro' cultivar (non-patented in the United States) and the 'Happy Returns' cultivar (non-patented in the United States) in the sense that it commonly possesses an extremely long and substantially continuous blooming season of up to approximately 110 days in USDA Hardiness Zone No. 7. Such blooming commonly begins during late May to early June and commonly ends during early to mid-October. This compares to a bloom period of less than about 30 days for over 99 percent of the hybrid Daylilies that are known to the inventor.

As indicated, 'Senset Returns' exhibits attractive gold-pastel flowers that readily can be distinguished from the orange-yellow flowers of the 'Stella D' Oro' cultivar and the medium yellow flowers of the 'Happy Returns' cultivar. To the best of the knowledge of the originator 'Sunset Returns' is the first long and substantially continuously blooming Daylily having flowers that exhibit a gold-pastel hue.

The new cultivar can form up to 5 or more fans per year. This compares to approximately 6 to 8 fans per year for the 'Stella D' Oro' cultivar and the 'Happy Returns' cultivar. Most Daylily cultivars form only approximately 2 to 3 fans per year. Also, the new cultivar commonly forms several scapes per fan during the flowering season, unlike most Daylilies that commonly produce only one scape per fan.

Asexual reproduction of the new cultivar by division was initially carried out on Sep. 18, 1986 at Bridgeton, N.J., U.S.A. At the time of such asexual reproduction the original plant of the new cultivar consisted of a clump of 5 fans that were phenotypically identical to each other. More specifically, the clump of the new cultivar was removed from the field and the fans were divided. It has been demonstrated that the characteristics of the new cultivar are firmly fixed and are well retained following this asexual reproduction.

'Sunset Returns' has not been observed under all possible environmental conditions to date. Accordingly, it is possible that the phenotype may vary somewhat with variations in the environment, such as temperature, light, day length, contact with pesticides, etc.

The new cultivar is being marketed beginning in 2002 while bearing the HAPPY EVER APPSTER trademark.

BRIEF DESCRIPTION OF THE PHOTOGRAPH

The accompanying photograph was prepared during the late summer, and shows as nearly true as it is reasonably possible to make the same in a color illustration of this character, the original plant and flower of the new cultivar of the present invention. The plant was approximately one year of age and was being grown outdoors in the field at Bridgeton, N.J., U.S.A.

FIG. 1—illustrates the plant clump with foliage, buds, and flowers in various stages of maturity.

DETAILED DESCRIPTION

The chart used in the identification of colors described herein is The R.H.S. Colour Chart of The Royal Horticultural Society, London, England. In some instances, more common color terms are provided and are to be accorded their usual dictionary significance. The original plant of the new cultivar is described when observed during early June 1996 when approximately one year of age and while growing at Bridgeton, N.J., U.S.A. under field growing conditions.

Plant:

*Height.*—Approximately 59 cm at an age of one year.

*Width.*—Approximately 44 cm at an age of one year.

*Foliage.*—Form: single stem, substantially erect scapes from a fan-shaped base having narrow arching, long, keeled, grass-like glabrous leaves that are two-ranked at the base of the scape. Quantity: abundant, with a mature plant commonly having approximately 11 leaves per fan. Leaf size: commonly approximately 1.25 cm in width on average and approximately 70 cm in length on average. Leaf shape: linear and long-keeled (as illustrated in FIG. 1) with entire margins. Texture: glabrous. Color: Green Group 137B on the upper surface and Green Group 137C on the under surface. Type: dormant with the plant losing all of its foliage during the winter.

*Scape.*—Color: Green Group 137B. Length: commonly approximately 58 cm on average. Diameter: approximately 6 mm.

*Disease resistance.*—Typical of Hemerocallis with no problems having been observed to date.

Inflorescence:

*Bud.*—Form: linear (as illustrated in FIG. 1). Size: on the day prior to opening commonly approximately 6.5 cm in length on average and approximately 1.2 cm in width on average. Color: Yellow-Green Group 144A. Opening rate: commonly approximately three hours on average. Outer tepal color: when sepals first divide, Yellow Group 11B. Peduncle character: rigid and sturdy. Peduncle diameter: approximately 4 mm. Peduncle color: Green Group 137B.

*Flower.*—Size: commonly has a diameter of approximately 8.5 on average and a depth of approximately 4 cm on average. Borne: singly on the branchlets of a sturdy erect rachis which is ramulose. Each scape commonly has at least two to three peduncles, each of which divides into approximately five to six pedicels. Blooms per scape: Commonly ranges from 1 to 2 each day. Tepalage: each flower consists of six perianth segments wherein there are three outer tepals and three inner tepals all in an imbricated arrangement. Outer tepal shape: modified oblanceolate with slightly undulated entire margins and an acuminate apex. Outer tepal texture: ribbed. Outer tepal size: commonly approximately 6.2 cm in length on average and approximately 2 cm in width on average. Outer tepal color: Naples Yellow, Yellow Group 11B on the upper surface and Yellow Group 12A on the under surface. Inner tepal shape: elliptic. Outer tepal apex: acute. Outer tepal margin: entire (smooth) with indentation. Inner tepal shape: elliptic. Inner tepal texture: highly corrugated. Inner tepal size: commonly approximately 6 cm in length on average and approximately 4 cm in width on average. Inner tepal color: Naples Yellow, Yellow Group 11B on the upper surface and Yellow Group 12A on the under surface. Blooming habit: the flowers commonly bloom substantially continuously and the scape commonly is substantially continuously in bloom for up to approximately 110 days per year in Hardiness Zone No. 7. Pedicel length: commonly approximately 5 mm. Pedicel diameter: commonly approximately 3 mm. Pedicel color: Yellow-Green Group 144A. Effects of weather: the flowers will withstand rain damage in view of the strength of the tepals. Lasting quality: commonly at least 16 hours. As with other Hemerocallis cultivars known to the inventor, the flower color eventually fades somewhat during the day with the natural effects of environmental conditions and ongoing maturity. Fragrance: light.

*Reproductive organs.*—Stamen number: six per flower. Stamen disposition: individually inserted at the summit of the perianth tube. Anther disposition: introrse. Anther size: approximately 0.7 cm in length. Anther color: Yellow-Orange Group 14A. Filament configuration: slender. Filament length: commonly approxi mately 4.5 cm on average. Filament color: Yellow Group 11A. Pollen color: Yellow-Orange Group 14A. Pistil number: one per flower. Style length: approximately 6.8 cm in length on average. Style color: Saffron Yellow, Yellow-Orange Group 19B. Stigma color: Saffron Yellow, Yellow-Orange Group 19B. Ovaries: three-celled, oblong, and becoming a loculiedally three-valved capsule.

*Fruit.*—Configuration: the seed pod is in the form of an ovoid capsule. Color: at maturity commonly is Green Group 137B. Fertility: the seeds are fertile.

Hardiness: U.S.D.A. Hardiness Zone Nos. 6 and 7.

I claim:

1. A new and distinct cultivar of Hemerocallis plant of the dormant type, substantially as herein shown and described, which:

(a) Forms attractive gold-pastel flowers having a substantial substance and a funnel-shaped form, (b) Possesses a long blooming season with substantially continuous blooming, (c) Exhibits a propensity to readily display a plurality of fans, and (d) Readily forms a plurality of scapes per fan over the flowering season.

* * * * *